(12) United States Patent
Doi et al.

(10) Patent No.: US 7,981,850 B2
(45) Date of Patent: *Jul. 19, 2011

(54) DETERGENT COMPOSITION

(75) Inventors: Yasuhiro Doi, Wakayama (JP); Masaki Inoue, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/521,460

(22) PCT Filed: Dec. 27, 2007

(86) PCT No.: PCT/JP2007/001480
§ 371 (c)(1), (2), (4) Date: Jun. 26, 2009

(87) PCT Pub. No.: WO2008/081591
PCT Pub. Date: Jul. 10, 2008

(65) Prior Publication Data
US 2010/0249003 A1    Sep. 30, 2010

(30) Foreign Application Priority Data
Dec. 28, 2006 (JP) ................. 2006-355716

(51) Int. Cl.
C11D 1/72 (2006.01)
C11D 1/835 (2006.01)
C11D 1/94 (2006.01)
C11D 3/37 (2006.01)

(52) U.S. Cl. ........ 510/119; 510/121; 510/123; 510/130; 510/473; 510/475; 510/504

(58) Field of Classification Search ........ 510/119, 510/121, 123, 130, 473, 475, 504
See application file for complete search history.

(56) References Cited

U.S. PATENT DOCUMENTS

| | | | |
|---|---|---|---|
| 5,876,705 A * | 3/1999 | Uchiyama et al. | 424/70.12 |
| 5,936,042 A | 8/1999 | Matsushima et al. | |
| 5,942,478 A * | 8/1999 | Lopes | 510/130 |
| 6,221,816 B1 | 4/2001 | Kasuga et al. | |
| 6,635,240 B1 | 10/2003 | Bolich, Jr. et al. | |
| 6,923,954 B2 | 8/2005 | Doi et al. | |
| 2005/0227880 A1 * | 10/2005 | Shiloach et al. | 510/130 |
| 2006/0079431 A1 * | 4/2006 | Lal et al. | 510/421 |
| 2006/0100127 A1 * | 5/2006 | Meier et al. | 510/499 |
| 2007/0128142 A1 | 6/2007 | Harrison et al. | |
| 2007/0238634 A1 | 10/2007 | Foland et al. | |
| 2008/0005853 A1 * | 1/2008 | Cottard et al. | 8/409 |

FOREIGN PATENT DOCUMENTS

| | | |
|---|---|---|
| FR | 2862235 A1 | 5/2005 |
| JP | 4-108723 A | 4/1992 |
| JP | 6-329866 A | 11/1994 |
| JP | 7-53991 A | 2/1995 |
| JP | 10-7808 A | 1/1998 |
| JP | 11-12594 A | 1/1999 |
| JP | 11-513687 A | 11/1999 |
| JP | 2004-277685 A | 10/2004 |
| JP | 2004277685 A * | 10/2004 |
| JP | 2007-197420 A | 8/2007 |
| WO | WO 96/32093 A1 | 10/1996 |
| WO | WO 97/14396 A1 | 4/1997 |
| WO | WO-2007/077668 A1 | 7/2007 |

OTHER PUBLICATIONS

Interview Summary dated Oct. 5, 2010 in U.S. Appl. No. 12/159,105.
Office Action dated Aug. 20, 2010 in U.S. Appl. No. 12/159,105.
European Application No. 07859665.7, European Search Report dated Apr. 5, 2011, pp. 1-5.

* cited by examiner

*Primary Examiner* — Lorna M Douyon
(74) *Attorney, Agent, or Firm* — Birch, Stewart, Kolasch & Birch, LLP

(57) ABSTRACT

Provided is a detergent composition that contains the following components (A), (B), and (C). Component (A) is at least one selected from the group consisting of cationic polymers and amphoteric polymers. Component (B) is a compound represented by the following formula (1): $R^1O\text{-}(AO)_n\text{-}R^2$ wherein $R^1$ represents a linear or branched alkyl or alkenyl group having from 8 to 10 carbon atoms, AO represents an alkyleneoxy group having from 2 to 4 carbon atoms, n means an average number of moles and stands for from 0.5 to 4, and $R^2$ represents a hydrogen atom or a methyl group. Component (C) is at least one selected from the group consisting of amphoteric surfactants and cationic surfactants. The detergent composition has a content of Component (A) from 5 to 40 wt. % and has Component (B) and Component (C) at a weight ratio (B)/(C) of from 0.5 to 2.5.

8 Claims, No Drawings

DETERGENT COMPOSITION

FIELD OF THE INVENTION

The present invention relates to a detergent composition containing a cationic polymer in high concentration, and also containing a specific alkylene oxide adduct (alkylene glycol ether) and surfactant.

BACKGROUND OF THE INVENTION

Detergent compositions are required to have various functions such as emulsifying or solubilizing actions on dirt components such as oil, and detergency. Among them, detergents for the skin, hair or dishes treated directly by human hands are required to have an improved feeling upon use during cleansing (good foamability and foam quality), during rinsing, and after drying, as opposed to industrial detergents used for metal cleansing.

For skin, hair or dish detergent compositions, therefore, various sorts of surfactants and feel-improving agents are used to enhance their foamability and improve a feeling upon use, respectively. In particular, when a cationic polymer is incorporated in a detergent for the skin or hair, it exhibits an excellent feel-improving function and therefore is used widely. On the other hand, a detergent composition containing a large amount of a cationic polymer has such a problem that its foamability fades away, and as a result, could lead to the deteriorative feeling upon use. This method is not constraint-free, as such.

A cationic polymer is usually provided in powder form so that (1) much time and labor must be spent for solubilizing it, (2) its handling ability is not so good due to solidification (blocking) caused by moisture absorption, and (3) dust generated from the powder worsens the working environment. With a view to overcoming these problems, a cationic polymer is used in the form of an aqueous solution. However, a high-molecular-weight cationic polymer having a good performance as a feel-improving agent tends to become highly viscous, thus making it impossible for the aqueous solution to be obtained in high concentration. The aqueous solution of a cationic polymer is therefore not useful from the standpoint of economy, for example, a transportation cost. Furthermore, the acceptable amount of a cationic polymer that can be added to a detergent composition is limited.

As a method of raising the concentration of a cationic polymer, replacement of a portion or whole of the aqueous solution with an organic solvent or oil component or emulsification of the aqueous solution is known. However, when added to a detergent composition, such an ingredient not only could cause a drastic reduction in foamability, but such an emulsion also has a problem with the composition stability.

As a method requiring no solvent, on the other hand, Patent Document 1 describes a method of using a specific cationic polymer in combination with an inorganic salt and Patent Document 2 describes a method of modifying a cationic polymer with an acid. These methods, however, cannot overcome the problem of reduction in foamability caused by the addition of a cationic polymer. Further, the addition of an inorganic salt or modification with an acid deteriorates the performance of the cationic polymer. Patent Document 3 discloses an example of adding a cationic polymer in high concentration while using a nonionic surfactant having an HLB of 12 or greater in combination. This method requires the additional use of a propellant for foaming. What is worse, this type of composition cannot generate sufficient foamability even if incorporated in a detergent.

Thus, from none of the prior art is it known to be able to obtain a detergent composition that is capable of containing therein a cationic polymer in high concentration and impairing neither foamability of the detergent nor feeling upon use even when incorporated in a detergent.

[Patent Document 1] JP-A-06-329866
[Patent Document 2] JP-A-10-7808
[Patent Document 3] WO96/32093

DISCLOSURE OF THE INVENTION

The present invention provides a detergent composition containing the following components (A), (B), and (C):

(A) at least one selected from the group consisting of cationic polymers and amphoteric polymers;

(B) a compound represented by the following formula (1):

$$R^1O\text{-}(AO)_n\text{—}R^2 \tag{1}$$

wherein $R^1$ represents a linear or branched alkyl or alkenyl group having from 8 to 10 carbon atoms, AO represents an alkyleneoxy group having from 2 to 4 carbon atoms, n means an average number of moles and stands for from 0.5 to 4, and $R^2$ represents a hydrogen atom or a methyl group; and (C) at least one selected from the group consisting of amphoteric surfactants and cationic surfactants, and the detergent composition having a content of Component (A) of from 5 to 40 wt. %; and having Component (B) and Component (C) at a weight ratio (B)/(C) of from 0.5 to 2.5.

DETAILED DESCRIPTION OF THE INVENTION

The present invention provides a detergent composition containing a high concentration of a cationic polymer capable of improving a feeling upon use, which is easy to produce, has good storage stability, causes no harm to foamability when incorporated in a detergent, and allows for an excellent feeling upon use.

As a result of intensive investigation, the present inventors have found that a detergent composition containing the above Components (A), (B), and (C) at a specific ratio enables a cationic polymer to be added thereto in high concentration and make itself stable, thereby imparting excellent foamability and feeling upon use.

According to the present invention, it is possible to obtain a detergent composition containing a high concentration of a cationic polymer capable of improving a feeling upon use, which is easy to produce, has good storage stability, causes no harm to foamability when incorporated in a detergent, and allows for an excellent feeling upon use.

Examples of the cationic polymer serving as Component (A) include one or more selected from the group consisting of the following (a) to (d):

(a) cationic cellulose derivatives,
(b) cationic guar gum derivatives,
(c) at least one compound selected from the group consisting of diallyl quaternary ammonium salt polymers and diallyl quaternary ammonium salt/acrylamide copolymers, and
(d) methacryloyloxyethyl quaternary ammonium salt/acrylamide copolymers.

Examples of the amphoteric polymer serving as Component (A) include one or more selected from the group consisting of the following (e) to (f):

(e) at least one selected from the group consisting of diallyl quaternary ammonium salt/acrylic acid copolymers and acrylic acid/diallyl quaternary ammonium salt/acrylamide copolymers, and (f) acrylic acid/methacrylamidopropyl quaternary ammonium salt/alkyl acrylate copolymers.

Cationic cellulose derivatives serving as Component (A) will hereinafter be described specifically.

The cationic cellulose derivative (a) is preferably represented by the following formula (VI):

[Chemical formula 1]

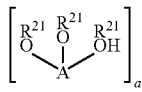

(VI)

In the formula (VI), A represents a residue of an anhydroglucose unit, a stands for an integer from 50 to 20000, each $R^{21}$ represents a substituent represented by the following formula (VII):

[Chemical formula 2]

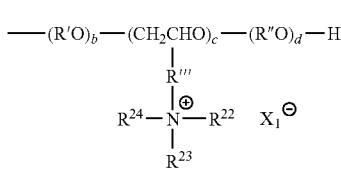

(VII)

In the formula (VII), R' and R" each represent an alkylene group having 2 or 3 carbon atoms, b stands for an integer from 0 to 10, c stands for an integer from 0 to 3, d stands for an integer from 0 to 10, R'" represents an alkylene or hydroxyalkylene group having from 1 to 3 carbon atoms, $R^{22}$, $R^{23}$, and $R^{24}$ may be the same or different and each represents an alkyl group, aryl group, or aralkyl group having up to 10 carbon atoms, or may form a heterocyclic ring together with the nitrogen atom in the formula, and $X_1$ represents an anion (such as chloride, bromide, iodide, sulfate, sulfonate, methyl sulfate, phosphate, or nitrate).

The degree of cationic substitution of the cationic cellulose is from 0.01 to 1, meaning that an average value of c per anhydroglucose unit is from 0.01 to 1, preferably from 0.02 to 0.5. The sum of b+d is from 1 to 3 on average. The degree of substitution not greater than 0.01 is not sufficient. On the other hand, it may be 1 or greater, but from the standpoint of reaction yield, it is preferably not greater than 1. With regard to $R^{22}$, $R^{23}$, and $R^{24}$, it is preferred that all of $R^{22}$, $R^{23}$, and $R^{24}$ be $CH_3$ group; or two of them be short-chain alkyl groups such as $CH_3$ group and the remaining one be a long-chain alkyl group having from 10 to 20 carbon atoms. The molecular weight of the cationic cellulose used herein ranges from about 100000 to 8000000.

Examples of the commercially available product include "Poise C-80H" (product of Kao Corporation) and "Polymer JR-400" (product of Dow Chemical).

The cationic guar gum derivative (b) serving as Component (A) will next be described specifically.

The cationic guar gum derivative is preferably represented by the following formula (VIII):

[Chemical formula 3]

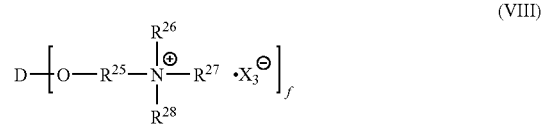

(VIII)

In the formula (VIII), D represents a guar gum residue, $R^{25}$ represents an alkylene group or a hydroxyalkylene group, $R^{26}$, $R^{27}$, and $R^{28}$ may be the same or different and each represents an alkyl, aryl, or aralkyl group having carbon atoms not greater than 10 or may form a heterocycle together with the nitrogen atom in the formula, $X_3$ represents an anion (such as chloride, bromide, iodide, sulfonate, methyl sulfate, phosphate, or sulfate), and f stands for a positive integer.

The degree of cationic substitution of the cationic guar gum derivative is preferably from 0.01 to 1. The cationic guar gum derivative having from 0.02 to 0.5 cationic group introduced into a sugar unit thereof is particularly preferred. Cationic polymers of such a type are described in JP-A-58-35640, JP-A-60-46158, and JP-A-58-53996. Examples of the commercially available products include those sold under the trade mark of Jaguar (product of Rhodia Inc.) including "Jaguar C-13C".

The diallyl quaternary ammonium salt polymers or diallyl quaternary ammonium salt/acrylamide copolymers (c) serving as Component (A) will next be described specifically.

The diallyl quaternary ammonium salt polymers or diallyl quaternary ammonium salt/acrylamide copolymers (c) are preferably represented by the following formula (IX) or (X).

[Chemical formula 4]

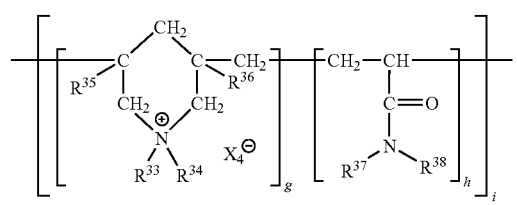

(IX)

[Chemical formula 5]

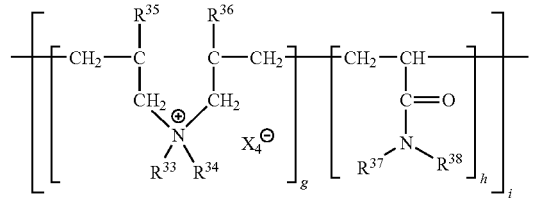

(X)

In the formulas (IX) and (X), $R^{33}$ and $R^{34}$ may be the same or different and each represents a hydrogen atom, an alkyl group (having from 1 to 18 carbon atoms), a phenyl group, an aryl group, a hydroxyalkyl group, an amidoalkyl group, a cyanoalkyl group, an alkoxyalkyl group, or a carboalkoxyalkyl group, $R^{35}$, $R^{36}$, $R^{37}$, and $R^{38}$ may be the same or different and each represents a hydrogen atom, a lower alkyl group (having from 1 to 3 carbon atoms), or a phenyl group, $X_4$ represents an anion (such as chloride, bromide, iodide, sulfonate, methyl sulfate, or sulfate), g stands for an integer from 1 to 50, h stands for an integer from 0 to 50, and i stands for an integer from 150 to 8000.

The molecular weight of the diallyl quaternary ammonium salt/acrylamide copolymer is from about 30000 to 2000000, preferably from 1000000 to 2000000.

For example, commercially available products thereof are sold under the trade mark of "Merquat" from Nalco Company and examples include "Merquat 100" and "Merquat 550".

The methacryloyloxyethyl quaternary ammonium salt/acrylamide copolymer (d) serving as Component (A) will next be described specifically.

The methacryloyloxyethyl quaternary ammonium salt/acrylamide copolymer (d) is preferably represented by the following formula (XI):

[Chemical formula 6]

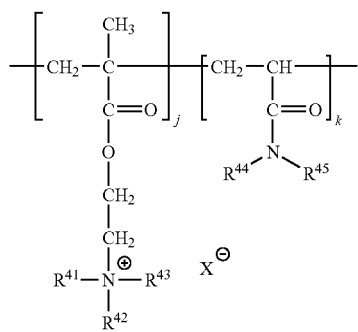

(XI)

In the formula (XI), $R^{41}$, $R^{42}$, and $R^{43}$ may be the same or different and each represents a hydrogen atom, an alkyl group (having from 1 to 18 carbon atoms), a phenyl group, an aryl group, a hydroxyalkyl group, an amidoalkyl group, a cyanoalkyl group, an alkoxyalkyl group, or a carboalkoxyalkyl group, $R^{44}$ and $R^{45}$ may be the same or different and each represents a hydrogen atom, a lower alkyl group (having from 1 to 3 carbon atoms), or a phenyl group, X represents an anion (such as chloride, bromide, iodide, sulfonate, methyl sulfate or sulfate), j stands for an integer from 5 to 20, and k stands for an integer from 80 to 95.

The molecular weight of the methacryloyloxyethyl quaternary ammonium salt/acrylamide copolymer is from about 1000000 to 10000000, preferably from 2000000 to 6000000.

For example, commercially available products thereof are sold under the trade mark of "Merquat" from Nalco Company and examples include "Merquat 5".

The at least one (e) selected from the group consisting of diallyl quaternary ammonium salt/acrylic acid copolymers and acrylic acid/diallyl quaternary ammonium salt/acrylamide copolymers serving as Component (A) will next be described specifically.

The at least one (e) selected from the group consisting of diallyl quaternary ammonium salt/acrylic acid copolymers and acrylic acid/diallyl quaternary ammonium salt/acrylamide copolymers is preferably represented by the following formula (XII).

[Chemical formula 7]

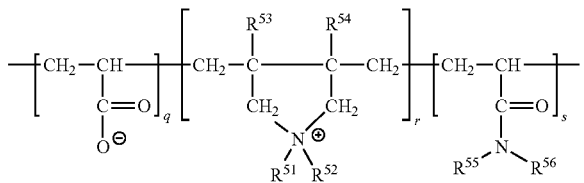

(XII)

In the formula (XII), $R^{51}$ and $R^{52}$ may be the same or different and each represents a hydrogen atom, an alkyl group (having from 1 to 18 carbon atoms), a phenyl group, an aryl group, a hydroxyalkyl group, an amidoalkyl group, a cyanoalkyl group, an alkoxyalkyl group, or a carboalkoxyalkyl group, $R^{53}$, $R^{54}$, $R^{55}$, and $R^{56}$ may be the same or different and each represents a hydrogen atom, a lower alkyl group (having from 1 to 3 carbon atoms), or a phenyl group, q stands for an integer from 5 to 25, r stands for an integer from 15 to 50, and s stands for an integer from 25 to 80.

The molecular weight of the diallyl quaternary ammonium salt/acrylic acid copolymer or acrylic acid/diallyl quaternary ammonium salt/acrylamide copolymer is preferably from 600000 to 3000000, more preferably from 1000000 to 2000000.

For example, commercially available products thereof are sold under the trade mark of "Merquat" from Nalco Company and examples include "Merquat 280" and "Merquat Plus 3330".

The acrylic acid/methacrylamidopropyl quaternary ammonium salt/alkyl acrylate copolymer (f) serving as Component (A) will next be described specifically.

The acrylic acid/methacrylamidopropyl quaternary ammonium salt/alkyl acrylate copolymer (f) is preferably represented by the following formula (XIII):

[Chemical formula 8]

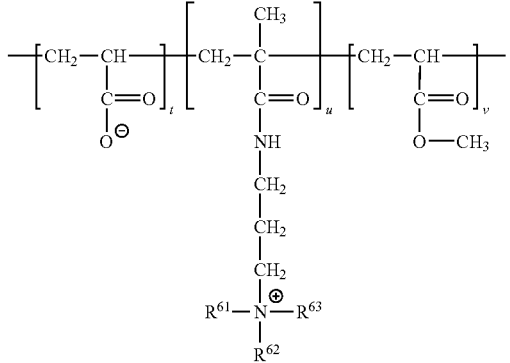

(XIII)

In the formula (XIII), $R^{61}$, $R^{62}$, and $R^{63}$ may be the same or different and each represents a hydrogen atom, an alkyl group (having from 1 to 18 carbon atoms), a phenyl group, an aryl group, a hydroxyalkyl group, an amidoalkyl group, a cyanoalkyl group, an alkoxyalkyl group, or a carboalkoxyalkyl group, t stands for an integer from 30 to 60, u stands for an integer from 30 to 60, and v stands for an integer from 5 to 20.

The molecular weight of the acrylic acid/methacrylamidopropyl quaternary ammonium salt/alkyl acrylate copolymer is from 600000 to 3000000, preferably from 1000000 to 2000000.

For example, commercially available products thereof are sold under the trade mark of "Merquat" from Nalco Company and examples include "Merquat 2001".

Component (A) is contained in the detergent composition in an amount of from 5 to 40 wt. %, preferably in an amount exceeding 5 wt. % but not greater than 40 wt. %. From the standpoint of suppressing thickening at the time of preparation and thereby improving handling properties and increasing the concentration of Component (A), it is contained preferably in an amount exceeding 5 wt. % but not greater than 30 wt. %, more preferably from 7 to 30 wt. %, still more preferably from 9 to 30 wt. %, still more preferably from 9 to 25 wt. %, even more preferably from 9 to 20 wt. %.

Component (B) is a compound represented by the above formula (1).

In the formula (1) of Component (B), $R^1$ represents a linear or branched alkyl or alkenyl group having from 8 to 10 carbon atoms. From the standpoint of odor reduction, it is preferably the linear alkyl group. $R^1$ is preferably a linear alkyl group having 8 carbon atoms from the standpoint of foamability. When $R^1$ is a mixture of the above alkyl groups, it contains the alkyl group having 8 carbon atoms in an amount of preferably 50 mol % or greater, more preferably 80 mol % or greater, even more preferably 98 mol % or greater.

In the formula (1) of Component (B), AO is an alkyleneoxy group having from 2 to 4 carbon atoms, preferably a propyleneoxy group (which will hereinafter be called "PO") and/or an ethyleneoxy group (which will hereinafter be called "EO"). The AO may contain PO and BO in block form or at random sequence, but the former one is preferred. From the standpoint of odor reduction, AO containing a PO block and an EO block arranged in this order is more preferred, with AO composed only of PO being even more preferred.

In the compound of the formula (1) as Component (B), n means the average number of moles and stands for the number of from 0.5 to 4. From the standpoint of foamability and odor reduction, it is preferably from 1.0 to 3.0, more preferably from 2.0 to 3.0, still more preferably from 2.0 to 2.8, even more preferably from 2.0 to 2.5.

In the formula (1), $R^2$ represents a hydrogen atom or a methyl group, with a hydrogen atom being preferred.

Component (B) is contained in the detergent composition in an amount of preferably from 5 to 60 wt. %, more preferably from 10 to 40 wt. %, even more preferably from 15 to 30 wt. % from the standpoint of foamability of the resulting detergent and an increase in the concentration of Component (A).

Component (C) is at least one surfactant selected from the group consisting of amphoteric surfactants and cationic surfactants.

When an anionic surfactant is used as Component (C), a too strong interaction between the cationic polymer and the anionic surfactant causes thickening and makes preparation difficult. When a nonionic surfactant is used as Component (C), on the other hand, the cationic polymer separates from the composition and precipitates therein, leading to deterioration in the stability of the composition. An amphoteric or cationic surfactant which causes an adequate interaction with the cationic polymer is necessary for the composition of the present invention. The amphoteric surfactant is preferred from the standpoint of improving foamability of the detergent obtained using the invention product.

The following are specific examples of the amphoteric and cationic surfactants.

Examples of the amphoteric surfactant include betaine surfactants. Of the betaine surfactants, imidazoline betaines, alkyldimethylaminoacetic acid betaines, fatty acid amidopropyl betaines, and alkylhydroxysulfobetaines are more preferred, with alkylcarboxymethylhydroxyethyl imidazolium betaines, fatty acid amidopropyl betaines, and alkylhydroxysulfobetaines being more preferred. As the fatty acid amidopropyl betaines and alkylhydroxysulfobetaines, those having an alkyl group having from 8 to 18 carbon atoms are preferred, with those having an alkyl group having from 10 to 16 carbon atoms being more preferred. Lauramidopropyl betaine, palm kernel oil fatty acid amidopropyl betaine, cocamidopropyl betaine, and laurylhydroxysulfo betaine are still more preferred.

Examples of the cationic surfactant include quaternary ammonium salts described in JP-A-00-178146 and represented by the following formula (3):

[Chemical formula 9]

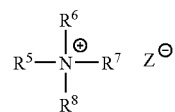

(3)

wherein at least one of $R^5$, $R^6$, $R^7$, and $R^8$ represents a linear or branched alkyl or alkenyl group which may be substituted with an alkoxy group having from 12 to 28 carbon atoms in total, preferably a linear or branched alkoxy group having from 16 to 28 carbon atoms, an alkenyloxy group, an alkanoylamino group, an alkenoylamino group, an alkanoyl group, or an alkanoyloxy group and the other(s) each represents a benzyl group, an alkyl group having from 1 to 5 carbon atoms, a hydroxyalkyl group, or a polyoxyethylene group in which the total number of moles added is not greater than 10, and $Z^-$ represents a halide ion or organic anion such as that selected from acetate, citrate, lactate, glycolate, phosphate, nitrate, sulfonate, sulfate, and alkyl sulfate groups.

Preferred examples of Compound (3) include compounds of the formula (3) wherein at least one of $R^5$, $R^6$, $R^7$, and $R^8$ represents an alkyl group which may be substituted with an alkoxy group having from 8 to 22 carbon atoms in total and the other(s) each represents a methyl, ethyl or benzyl group. Preferred specific examples include mono(long chain) alkyltrimethylammonium chlorides such as stearyltrimethylammonium chloride and octadecyloxypropyltrimethylammonium chloride and di(long chain) alkyldimethylammonium chlorides such as distearyldimethylammonium chloride and branched dialkyldimethylammonium chloride.

Component (C) is contained in the detergent composition in an amount of from 5 to 60 wt. %, more preferably from 10 to 40 wt. %, still more preferably from 15 to 30 wt. % from the standpoints of foamability of a detergent obtained using the composition and an increase in the concentration of the polymer.

With regards to a ratio of Component (B) to Component (C), a (B)/(C) weight ratio is preferably from 0.5 to 2.5, more preferably from 0.6 to 2.0, still more preferably from 0.6 to 1.7, even more preferably from 0.8 to 1.2 from the standpoint of stability of the resulting detergent composition.

With regard to a ratio of Component (A) to Components (B)+(C), a (A)/[(B)+(C)] weight ratio is preferably from 0.10 to 2.0, more preferably from 0.15 to 1.5, more preferably from 0.20 to 1.0, even more preferably from 0.25 to 0.8 from the standpoint of an increase in the concentration of the cationic polymer and foamability of a detergent obtained using the composition.

It is preferred to add Component (D) further to the detergent composition of the present invention from the standpoint of improving its handling properties at the time of preparation and improving stability.

Component (D) is a solvent represented by the following formula (2):

$$R^3O\text{-}(AO)_m\text{—}R^4 \qquad (2)$$

wherein $R^3$ and $R^4$ each represents a hydrogen atom or a methyl group and AO represents an alkyleneoxy group having from 2 to 4 carbon atoms, and m stands for an integer from 1 to 3. In the formula (2), $R^3$ and $R^4$ each represents a hydrogen atom or a methyl group, AO represents an alkyleneoxy group having from 2 to 4 carbon atoms, and m stands for an integer from 1 to 3.

It is preferred that either one of $R^3$ and $R^4$ represent a hydrogen atom and it is more preferred that both represent a hydrogen atom.

AO represents an alkyleneoxy group having from 2 to 4 carbon atoms, preferably a propyleneoxy group (which will hereinafter be called "PO") and/or ethyleneoxy group (which will hereinafter be called "EO), more preferably PO.

The reference numeral m preferably stands for 1 or 2.

Preferred examples of Component (D) include propylene glycol, dipropylene glycol, and 1,2-butanediol.

Component (D) is contained in the detergent composition preferably in an amount of from 1 to 20 wt. %, more preferably from 2 to 15 wt. %, even more preferably from 3 to 10 wt. % from the standpoint of foamability and improvement in stability.

The detergent composition of the present invention may contain an anionic surfactant, a nonionic surfactant other than Component (B) of the present invention, and an oil component without impairing stability of the composition or the feeling upon use and foamability of a detergent obtained using the detergent composition.

As the anionic surfactant, sulfate, sulfonate, carboxylate, phosphate, and amino acid based anionic surfactants are preferred. Specific examples include alkyl sulfates, polyoxyalkylene alkyl ether sulfates, polyoxyalkylene alkenyl ether sulfates, alkyl sulfosuccinates, polyoxyalkylene alkyl sulfosuccinates, polyoxyalkylene alkyl phenyl ether sulfates, alkane sulfonates, acyl isethionates, acyl methyl taurates, higher fatty acid salts, polyoxyalkylene alkyl ether acetates, alkyl phosphates, polyoxyalkylene alkyl ether phosphates, acyl glutamates, alanine derivatives, glycine derivatives, and arginine derivatives.

Of these, polyoxyethylene alkyl ether sulfates, polyoxyethylene alkenyl ether sulfates, alkyl sulfates, higher fatty acid salts, polyoxyalkylene alkyl ether acetates, alkyl phosphates, and polyoxyalkylene alkyl ether phosphates are preferred, with those represented by the following formula (4) or (5) being more preferred.

$$R^9\text{—}O(CH_2CH_2O)_pSO_3M \qquad (4)$$

$$R^{10}\text{—}OSO_3M \qquad (5)$$

wherein $R^9$ represents an alkyl or alkenyl group having from 10 to 18 carbon atoms, $R^{10}$ represents an alkyl group having from 10 to 18 carbon atoms, M represents an alkali metal, alkaline earth metal, ammonium, alkanolamine, or basic amino acid, and p means an average number of moles of ethylene oxide and stands for 1 to 5.

Examples of the nonionic surfactant other than Component (B) of the present invention include polyoxyalkylene sorbitan fatty acid esters, polyoxyalkylene sorbitol fatty acid esters, polyoxyalkylene glycerin fatty acid esters, polyoxyalkylene fatty acid esters, polyoxyalkylene alkyl ethers, polyoxyalkylene alkyl phenyl ethers, polyoxyalkylene (hydrogenated) castor oils, sucrose fatty acid esters, polyglycerin alkyl ethers, polyglycerin fatty acid esters, fatty acid alkanolamides, and alkyl glycosides. Of these, polyoxyalkylene alkyl ethers, alkyl glycosides, polyoxyalkylene fatty acid ($C_{8-20}$ esters, polyoxyethylene sorbitan fatty acid esters, polyoxyethylene hydrogenated castor oils, and fatty acid alkanolamides are preferred. The polyoxyalkylene alkyl ethers are preferably polyoxyethylene alkyl ethers, polyoxypropylene alkyl ethers and polyoxyethylene/polyoxypropylene alkyl ethers. The alkyl glycosides are preferably those having an alkyl group with from 8 to 14 carbon atoms and a degree of condensation of sugar (glucose) of from 1 to 2. The fatty acid alkanolamides are preferably those having an acyl group with from 8 to 18 carbon atoms, more preferably those having an acyl group with from 10 to 16 carbon atoms. They may be either monoalkanolamides or dialkanolamides, but those having a hydroxyalkyl group with from 2 to 3 carbon atoms are preferred. Specific examples of the fatty acid alkanolamide include oleic acid diethanolamide, palm kernel oil fatty acid diethanolamide, coconut fatty acid diethanolamide, lauric acid diethanolamide, polyoxyethylene coconut fatty acid monoethanolamide, coconut fatty acid monoethanolamide, lauric acid monoisopropanolamide, lauric acid monoethanolamide, palm kernel oil fatty acid methyl ethanolamide, and coconut fatty acid methyl ethanolamide.

Examples of the oil component include higher alcohols, silicones, ester oils, hydrocarbons, glycerides, vegetable oils, animal oils, lanoline derivatives, and higher fatty acid esters. Of these, higher alcohols, ester oils, and/or silicones are preferred, with higher alcohols and/or silicones being more preferred.

The detergent composition of the present invention may further contain, as needed, a humectant, polysaccharide, polypeptide, pearling agent, solvent other than Component (D), liquid-crystal forming base, colorant, perfume, propellant, chelating agent such as edetate or citrate, pH regulator, antiseptic, antidandruff, and the like.

The detergent composition of the present invention can be prepared by stirring and mixing Components (A), (B), and (C) at from 20 to 70° C. It is suited for application to the skin or hair. Although no particular limitation is imposed on the form of the composition, it is preferably in the form of a liquid, paste, or cream. When the composition is prepared, a solvent is preferably used. As the solvent, water or Component (D) is more preferred.

A 20-fold diluted solution of the detergent composition of the present invention has a pH at 25° C. of preferably from 3 to 10, more preferably from 4 to 9.

The detergent composition of the present invention is preferably used for the preparation of a skin cleanser or hair shampoo.

(Application to Detergent)

The detergent composition according to the present invention can be used as a detergent after dilution with water or can be incorporated as a component of a detergent, for example, a skin cleanser such as face wash or body shampoo, a hair shampoo, or a dish wash after addition of a surfactant or conditioning agent. Preferably, it can be incorporated as a component of a skin cleanser or hair shampoo. A detergent containing the detergent composition may contain arbitrary components, depending on its using purpose. Examples of the arbitrary component include anionic surfactants, nonionic surfactants, surfactants such as Component (C) of the present invention, oil components, Components (A) of the present invention, and cationic polymers other than Component (A) of the present invention which are typically incorporated in the above detergents. The surfactant to be used for the detergent may be the same as or different from Component (B) or Component (C).

Examples of the cationic polymer other than Component (A) of the present invention include cationic-group-containing copolymers such as "Sofcare KG-301W" (product of Kao Corporation).

As another arbitrary component, other components to be typically incorporated in a detergent can be added as needed without impairing the advantage of the present invention and examples of them include water soluble polymers, e.g., polysaccharides such as methyl cellulose, hydroxyethyl cellulose, carboxyvinyl polymers, and xanthan gum; viscosity regulators such as polyoxyalkylene sorbitan ester, polyoxyethylene glycol distearate, and ethanol; chelating agents such as ethylenediaminetetraacetic acid (EDTA) and phosphonates; antiseptics such as methylparaben and butylparaben; active components such as vitamins and precursors thereof; animal or vegetable extracts such as lecithin and gelatin, or derivatives thereof; finely divided polymers such as nylon and polyethylene; anti-inflammatory agents such as dipotassium glycyrrhizinate; bactericides or anti-dandruffs such as triclosan, triclocarban, octopirox, and zinc pyrithione; antioxidants such as dibutylhydroxytoluene; pearling agents; ultraviolet absorbers; pH regulators; colorants; perfumes; and water.

The detergent containing the detergent composition according to the present invention can be prepared in a manner known per se in the art. A ratio of the surfactant to be added as an arbitrary component and the detergent composition, that is, a surfactant/detergent composition weight ratio is from 1 to 60, more preferably from 5 to 30 from the standpoint of foamability and touch feel.

One or more of the detergent compositions of the present invention may be used A content of the detergent composition in a skin cleanser or hair shampoo composition is preferably from 0.5 to 12 wt. %, more preferably from 2 to 10 wt. % in the whole composition from the standpoint of foam quality, touch feel, and conditioning effect.

The form of the skin cleanser or hair shampoo composition is not particularly limited and it can be provided in any form such as liquid, paste, cream, solid or powder. Of these, liquid form, paste form, and cream form are preferred, with the liquid form being more preferred. When the skin cleanser or hair shampoo composition is provided in liquid form, use of water as a liquid medium is preferred.

EXAMPLES

Example 1

Compositions (containing a cationic polymer, an alkylene glycol listed in Table 1 or 2, and the like) shown in Table 3 or 4 were prepared as detergent compositions and they were evaluated for (1) state at the time of preparation and (2) stability. In addition, (3) feeling upon use and foamability of a detergent containing the resulting detergent composition were evaluated.

(1) State at the Time of Preparation

The state of the detergent composition was macroscopically evaluated based on the following criteria:
A: Neither thickening nor gelation occurs during mixing, which facilitates mixing.
B: Gelation occurs during mixing, which prevents smooth mixing.
C: Thickening occurs and prevents mixing.

(2) Stability
(Stability Test at 40° C.)

After the detergent composition was put in a glass bottle (having a height of 9.5 cm and inner diameter of 4.5 cm) and stored at 40° C. for 10 days, it was taken out from the condition of 40° C. and left to stand at room temperature for one hour. The resulting composition was compared with another composition stored at room temperature (25° C.). The appearance was macroscopically evaluated based on the following criteria.
A: The composition has excellent stability without any change.
B: The composition has good stability, though undergoing a slight and insignificant change.
C: The composition causes precipitation and is separated.

(3) Test on Foamability and Feeling Upon use

An aqueous solution was prepared by adding and dissolving the detergent composition in 15 wt. % sodium polyoxyethylene alkyl ether sulfate (SLES) (average number of moles of ethylene oxide: 2) ("Emal 270 L", product of Kao Corporation) to give a polymer content of 0.3 wt. %.

A panel of ten experts was asked to wash their hands and arms with 1 ml of the resulting aqueous solution dropped to their palms and evaluate the foam amount, touch feel during washing, and finger combability during rinsing based on the following criteria.

(Foam Amount)
4: A foam amount is very large.
3: A foam amount is large.
2: A foam amount is slightly large.
1: A foam amount is small.

(Touch Feel During Washing)
4: It provides a good touch feel.
3: It provides a little good touch feel.
2: It provides a slightly bad touch feel.
1: It provides a bad touch feel.

(Touch Feel During Rinsing)
4: It provides a good touch feel.
3: It provides a little good touch feel.
2: It is a little inferior in touch feel.
1: It is inferior in touch feel.

An average of the scores of ten experts was determined and the aqueous solution having a score of 3.6 or greater, from 2.6 to 3.5, from 1.6 to 2.5, and 1.5 or less were ranked as A, B, C, and D, respectively.

TABLE 1

| $R^1O\text{-}(AO)_n\text{-}R^2$ | $R^{1*}$ | $R^2$ | $(AO)_n$ |
|---|---|---|---|
| Alkylene glycol ether 1 | $C_8$ | H | $(PO)_{2.3}$ |
| Alkylene glycol ether 2 | $C_8$ | H | $(EO)_2$ |
| Alkylene glycol ether 3 | 2-ethylhexyl | H | $(EO)_{2.5}$ |
| Alkylene glycol ether 4 | $C_8/C_{10}$ (molar ratio: 1/1) | H | $(PO)_{1.8}$ |

$C_8$: n-octyl, $C_{10}$: n-decyl

TABLE 2

| $R^1O$-$(AO)_n$—$R^2$ | $R^{1*}$ | $R^2$ | $(AO)_n$ |
|---|---|---|---|
| Alkylene glycol ether 5 | $C_{12}$ | H | $(EO)_2(PO)_2(EO)_3$ |
| Alkylene glycol ether 6 | $C_{10}$ | H | $(PO)_1(EO)_6$ |
| Alkylene glycol ether 7 | $C_3$ | H | $(PO)_2$ |

*$C_{12}$: n-dodecyl, $C_{10}$: n-decyl, $C_3$: n-propyl

TABLE 3

| Component | Detergent composition (wt. %) | Invention products 1 | 2 | 3 | 4 | 5 | 6 | 7 | 8 | 9 | 10 |
|---|---|---|---|---|---|---|---|---|---|---|---|
| (A) | Cationic polymer 1[1] | 16.0 | 20.0 | 25.0 | 9.0 | 9.0 | 9.0 | 9.0 | 9.0 | 9.0 | |
| | Cationic polymer 2[2] | | | | | | | | | | 9.0 |
| | Cationic polymer 3[3] | | | | | | | | | | |
| | Amphoteric polymer 4[4] | | | | | | | | | | |
| (B) | Alkylene glycol ether 1 | 18.0 | 17.0 | 15.0 | 17.0 | 21.3 | 12.5 | | | | 19.0 |
| | Alkylene glycol ether 2 | | | | | | | 20.0 | | | |
| | Alkylene glycol ether 3 | | | | | | | | 20.0 | | |
| | Alkylene glycol ether 4 | | | | | | | | | 20.0 | |
| | Alkylene glycol ether 5 | | | | | | | | | | |
| | Alkylene glycol ether 6 | | | | | | | | | | |
| | Alkylene glycol ether 7 | | | | | | | | | | |
| (C) | Laurylhydroxysulfo betaine[5] | 18.0 | 17.0 | 15.0 | 17.0 | 12.5 | 21.3 | 20.0 | 20.0 | 20.0 | 19.0 |
| | Cocamidopropyl betaine[6] | | | | | | | | | | |
| | Cetyl trimethyl ammonium chloride[7] | | | | | | | | | | |
| | Lauryldimetylamine oxide[8] | | | | | | | | | | |
| | Polyoxyethylene cetyl ether (EO = 13, HLB: 14.2) | | | | | | | | | | |
| | Sodium polyoxyethylene lauryl ether sulfate[9] | | | | | | | | | | |
| (D) | Propylene glycol | | | | | | | | | | |
| | Dipropylene glycol | | | | | | | | | | |
| | 1,3-Butanediol | | | | | | | | | | |
| | Purified water | Balance | Balance | Balance | Balance | Balance | Balance | Balance | Balance | Balance | Balance |
| | (B)/(C) | 1.0 | 1.0 | 1.0 | 1.0 | 1.7 | 0.6 | 1.0 | 1.0 | 1.0 | 1.0 |
| | (A)/[(B) + (C)] | 0.4 | 0.6 | 0.8 | 0.3 | 0.3 | 0.3 | 0.2 | 0.2 | 0.2 | 0.2 |
| | State at the time of preparation | A | A | A | A | A | A | A | A | A | A |
| | Solution stability | B | B | B | B | B | B | B | B | B | B |
| Evaluation results after addition of 0.3 wt % as Component (A) to 15 wt. % SLES | Foam amount | A | A | A | A | A | A | B | A | A | B |
| | Touch feel during washing | A | A | A | A | A | A | A | A | A | A |
| | Touch feel during rinsing | A | A | A | A | B | A | A | B | A | A |

| Component | Detergent composition (wt. %) | Invention products 11 | 12 | 13 | 14 | 15 | 16 | 17 | 18 | 19 | 20 |
|---|---|---|---|---|---|---|---|---|---|---|---|
| (A) | Cationic polymer 1[1] | | 16.0 | 16.0 | 16.0 | 16.0 | 20.0 | 9.0 | 9.0 | | 30.0 |
| | Cationic polymer 2[2] | | | | | | | | | | |
| | Cationic polymer 3[3] | 9.0 | | | | | | | | | |
| | Amphoteric polymer 4[4] | | | | | | | | | 9.0 | |
| (B) | Alkylene glycol ether 1 | 19.0 | 18.2 | 18.2 | 18.2 | 18.0 | 20.0 | 20.0 | 30.0 | 20.0 | 15.0 |
| | Alkylene glycol ether 2 | | | | | | | | | | |
| | Alkylene glycol ether 3 | | | | | | | | | | |
| | Alkylene glycol ether 4 | | | | | | | | | | |
| | Alkylene glycol ether 5 | | | | | | | | | | |
| | Alkylene glycol ether 6 | | | | | | | | | | |
| | Alkylene glycol ether 7 | | | | | | | | | | |
| (C) | Laurylhydroxysulfo betaine[5] | 19.0 | | | | 18.0 | 20.0 | 20.0 | 18.0 | 20.0 | 15.0 |
| | Cocamidopropyl betaine[6] | | 18.2 | | | | | | | | |
| | Cetyl trimethyl ammonium chloride[7] | | | 18.2 | | | | | | | |
| | Lauryldimetylamine oxide[8] | | | | 18.2 | | | | | | |
| | Polyoxyethylene cetyl ether (EO = 13, HLB: 14.2) | | | | | | | | | | |
| | Sodium polyoxyethylene lauryl ether sulfate[9] | | | | | | | | | | |
| (D) | Propylene glycol | | | | | | 7.0 | | | | |
| | Dipropylene glycol | | | | | | | 5.0 | 5.0 | 5.0 | 7.0 |
| | 1,3-Butanediol | | | | | 5.0 | | | | | |
| | Purified water | Balance | Balance | Balance | Balance | Balance | Balance | Balance | Balance | Balance | Balance |
| | (B)/(C) | 1.0 | 1.0 | 1.0 | 1.0 | 1.0 | 1.0 | 1.0 | 1.7 | 1.0 | 1.0 |

TABLE 3-continued

|  |  |  |  |  |  |  |  |  |  |  |  |
|---|---|---|---|---|---|---|---|---|---|---|---|
|  | (A)/[(B) + (C)] | 0.2 | 0.4 | 0.4 | 0.4 | 0.4 | 0.5 | 0.2 | 0.2 | 0.2 | 1.0 |
|  | State at the time of preparation | A | A | A | A | A | A | A | A | A | A |
|  | Solution stability | B | B | B | B | A | A | A | A | A | A |
| Evaluation results after addition of 0.3 wt % as Component (A) to 15 wt. % SLES | Foam amount | A | A | A | A | A | A | A | A | A | A |
|  | Touch feel during washing | A | A | A | A | A | A | A | A | A | A |
|  | Touch feel during rinsing | A | A | A | A | A | A | A | A | A | A |

[1] "Merquat 2200" (product of Nalco Company)
[2] "Poise C-80M" (product of Kao Corporation)
[3] "JAGUAR C-13S" (product of Sansho Co., Ltd.)
[4] "Merquat 3330" (product of Nalco Company)
[5] "Amphitol 20HD" (product of Kao Corporation)
[6] "Amphitol 55AB" (product of Kao Corporation)
[7] "Quartamin 60W" (product of Kao Corporation)
[8] "Amphitol 20N" (product of Kao Corporation)
[9] Average number of moles of ethylene oxide: 2

TABLE 4

| Component | Detergent composition (wt. %) | Comparative products 1 | 2 | 3 | 4 | 5 | 6 |
|---|---|---|---|---|---|---|---|
| (A) | Cationic polymer 1[1] | 16.0 | 16.0 | 16.0 | 16.0 | 16.0 | 9.0 |
|  | Cationic polymer 2[2] |  |  |  |  |  |  |
|  | Cationic polymer 3[3] |  |  |  |  |  |  |
|  | Amphoteric polymer 4[4] |  |  |  |  |  |  |
| (B) | Alkylene glycol ether 1 |  |  |  |  | 18.0 | 25.5 |
|  | Alkylene glycol ether 2 |  |  |  |  |  |  |
|  | Alkylene glycol ether 3 |  |  |  |  |  |  |
|  | Alkylene glycol ether 4 |  |  |  |  |  |  |
| (C) | Alkylene glycol ether 5 |  | 18.0 |  | 18.0 |  | 8.5 |
|  | Alkylene glycol ether 6 |  |  |  |  |  |  |
|  | Alkylene glycol ether 7 |  |  |  |  |  |  |
| (C) | Laurylhydroxysulfo betaine[5] |  |  |  |  |  |  |
|  | Cocamidepropyl betaine[6] |  |  |  |  |  |  |
|  | Cetyl trimethyl ammonium chloride[7] |  |  |  |  |  |  |
|  | Lauryldimetylamine oxide[8] |  |  |  |  |  |  |
|  | Polyoxyethylene cetyl ether (EO = 13, HLB: 14.2) |  |  |  |  |  |  |
|  | Sodium polyoxyethylene lauryl ether sulfate[9] |  |  |  |  |  |  |
| (D) | Propylene glycol |  |  |  |  |  |  |
|  | Dipropylene glycol |  |  | 5.0 | 5.0 |  |  |
|  | 1,3-Butanediol |  |  |  |  |  |  |
|  | Purified water | Balance | Balance | Balance | Balance | Balance | Balance |
|  | (B)/(C) | — | — | — | — | — | 3.0 |
|  | (A)/[(B) + (C)] | — | 0.9 | — | 0.9 | 0.9 | 0.3 |
|  | State at the time of preparation | B | B | B | A | A | A |
|  | Solution stability | B | C | C | C | C | C |
| Evaluation results after addition of 0.3 wt. % as Component (A) to 15 wt. % SLES | Foam amount | D | C | D | C | B | D |
|  | Touch feel during cleansing | C | B | B | B | B | C |
|  | Touch feel during rinsing | B | B | B | B | B | B |

| Component | Detergent composition (wt. %) | Comparative products 7 | 8 | 9 | 10 | 11 | 12 |
|---|---|---|---|---|---|---|---|
| (A) | Cationic polymer 1[1] | 9.0 | 16.0 | 16.0 | 16.0 | 16.0 | 16.0 |
|  | Cationic polymer 2[2] |  |  |  |  |  |  |
|  | Cationic polymer 3[3] |  |  |  |  |  |  |
|  | Amphoteric polymer 4[4] |  |  |  |  |  |  |
| (B) | Alkylene glycol ether 1 | 8.0 |  |  |  | 18.0 | 18.0 |
|  | Alkylene glycol ether 2 |  |  |  |  |  |  |
|  | Alkylene glycol ether 3 |  |  |  |  |  |  |
|  | Alkylene glycol ether 4 |  |  |  |  |  |  |
| (C) | Alkylene glycol ether 5 | 25.5 | 18.0 | 18.0 | 18.0 |  |  |
|  | Alkylene glycol ether 6 |  |  |  |  |  |  |
|  | Alkylene glycol ether 7 |  |  |  |  |  |  |
| (C) | Laurylhydroxysulfo betaine[5] |  |  |  |  |  |  |
|  | Cocamidepropyl betaine[6] |  |  |  |  |  |  |
|  | Cetyl trimethyl ammonium chloride[7] |  |  |  |  |  |  |
|  | Lauryldimetylamine oxide[8] |  |  |  |  |  |  |
|  | Polyoxyethylene cetyl ether |  |  |  |  | 18.0 |  |

TABLE 4-continued

|  |  |  |  |  |  |  |  |
|---|---|---|---|---|---|---|---|
|  | (EO = 13, HLB: 14.2) |  |  |  |  |  |  |
|  | Sodium polyoxyethylene |  |  |  |  |  | 18.0 |
|  | lauryl ether sulfate[9)] |  |  |  |  |  |  |
| (D) | Propylene glycol |  |  |  |  |  |  |
|  | Dipropylene glycol |  |  |  |  |  |  |
|  | 1,3-Butanediol |  |  |  |  |  |  |
|  | Purified water | Balance | Balance | Balance | Balance | Balance | Balance |
|  | (B)/(C) | 0.3 | 1.0 | 1.0 | 1.0 | 1.0 | 1.0 |
|  | (A)/[(B) + (C)] | 0.3 | 0.4 | 0.4 | 0.4 | 0.4 | 0.4 |
|  | State at the time of preparation | A | A | A | A | A | C |
|  | Solution stability | C | C | C | C | C | — |
| Evaluation results | Foam amount | D | C | C | D | D | — |
| after addition of 0.3 wt. | Touch feel during cleansing | C | B | C | C | C | — |
| % as Component (A) | Touch feel during rinsing | D | B | B | B | D | — |
| to 15 wt. % SLES |  |  |  |  |  |  |  |

[1)]"Merquat 2200" (product of Nalco Company)
[2)]"Poise C-80M" (product of Kao Corporation)
[3)]"JAGUAR C-13S" (product of Sansho Co., Ltd.)
[4)]"Merquat 3330" (product of Nalco Company)
[5)]"Amphitol 20HD" (product of Kao Corporation)
[6)]"Amphitol 55AB" (product of Kao Corporation)
[7)]"Quartamin 60W" (product of Kao Corporation)
[8)]"Amphitol 20N" (product of Kao Corporation)
[9)]Average number of moles of ethylene oxide: 2
* In the above table, a (B)/(C) weight ratio and an (A)/[(B) + (C)] weight ratio are shown by using Alkylene glycols 5 to 7 as Component (B) in Comparative products 8 to 10 and by using polyoxyethylene cetyl ether (EO-13, HLB: 14.2) or sodium polyoxyethylene lauryl ether sulfate (n = 2 moles) as Component C in Comparative products 11 and 12.

Example 2

A hair shampoo having the following composition was prepared by adding a surfactant and the like to Invention product 1.

| (Components) | (wt. %) |
|---|---|
| Invention product 1 | 4.4 |
| Ammonium polyoxyethylene (1) lauryl ether sulfate | 12.0 |
| Lauric acid monoethanolamide | 0.8 |
| Silicone* | 1.0 |
| Perfume, methylparaben | q.s. |
| Purified water | Balance |
| Total | 100 |

*Silicone: "BY22-60", product of Dow Corning Toray

The hair shampoo thus obtained had good foamability and provided an excellent feeling upon use with smooth finger combability during from shampooing to drying.

Example 3

A hair shampoo having the following composition was prepared by adding a surfactant and the like to Invention product 9.

| (Components) | (wt. %) |
|---|---|
| Invention product 9 | 4.0 |
| Sodium polyoxyethylene (3) lauryl ether sulfate | 18.0 |
| Lauric acid monoethanolamide | 0.8 |
| Silicone* | 1.0 |
| Perfume, methylparaben | q.s. |
| Purified water | Balance |
| Total | 100 |

*Silicone: "BY22-60", product of Dow Corning Toray

The hair shampoo thus obtained had good foamability and provided an excellent feeling upon use with smooth finger combability during from shampooing to drying.

Example 4

A body shampoo having the following composition was prepared by adding a surfactant and the like to Invention product 8.

| (Components) | (wt. %) |
|---|---|
| Invention product 8 | 5.6 |
| Sodium polyoxyethylene (2) lauryl ether sulfate* | 16.0 |
| Amidopropyl betaine** | 2.0 |
| Glycerin | 3.0 |
| Perfume, methylparaben | q.s. |
| Purified water | Balance |
| Total | 100 |

*"Emal 270J", product of Kao Corporation
**"Amphitol 20AB", product of Kao Corporation The body shampoo thus obtained had good foamability, provided foam with a good foam quality during shampooing, and had an excellent feeling upon use while leaving a moisturized feel on the skin even after drying.

Example 5

A body shampoo having the following composition was prepared by adding a surfactant and the like to Invention product 17.

| (Components) | (wt. %) |
|---|---|
| Invention product 17 | 3.3 |
| Lauryl phosphate* | 30.0 |
| Laurylhydroxysulfo betaine** | 2.0 |
| Sorbitol | 5.0 |
| Perfume, methylparaben | q.s. |
| Purified water | Balance |
| Total | 100 |

*"Prioly B-650", product of Kao Corporation
**"Amphitol 20HD", product of Kao Corporation The body shampoo thus obtained had good foamability, provided foam with a good foam quality during shampooing, and had an excellent feeling upon use while leaving a moisturized feel on the skin even after drying.

The invention claimed is:

1. A detergent composition comprising the following components (A), (B), and (C):
   (A) at least one selected from the group consisting of cationic polymers and amphoteric polymers;
   (B) a compound represented by the following formula (1):

$$R^1O\text{-}(AO)_n\text{-}R^2 \qquad (1)$$

wherein $R^1$ represents a linear or branched alkyl or alkenyl group having from 8 to 10 carbon atoms, AO represents an alkyleneoxy group having from 2 to 4 carbon atoms, n means an average number of moles and stands for from 0.5 to 4, and $R^2$ represents a hydrogen atom; and
   (C) at least one selected from the group consisting of amphoteric surfactants and cationic surfactants, and
   the detergent composition having a content of Component (A) from 5 to 40 wt. % and Component (B) and Component (C) at a weight ratio (B)/(C) of from 0.6 to 1.7.

2. The detergent composition according to claim 1, wherein Component (A) is at least one selected from the group consisting of (a) cationic cellulose derivatives, (b) cationic guar gum derivatives, (c) at least one selected from the group consisting of diallyl quaternary ammonium salt polymers and diallyl quaternary ammonium salt acrylamide copolymers, (d) methacryloyloxyethyl quaternary ammonium salt/acrylamide copolymers, (e) at least one selected from the group consisting of diallyl quaternary ammonium salt/acrylic acid copolymers and acrylic acid/diallyl quaternary ammonium salt/acrylamide copolymers, and (f) acrylic acid/methacrylamidopropyl quaternary ammonium salt/alkyl acrylate copolymers.

3. The detergent composition according to claim 1 or 2, further comprising Component (D) represented by the following formula (2):

$$R^3O\text{-}(AO)_m\text{-}R^4 \qquad (2)$$

wherein $R^3$ and $R^4$ each represent a hydrogen atom or a methyl group, AO represents an alkyleneoxy group having from 2 to 4 carbon atoms, and m stands for an integer from 1 to 3.

4. The detergent composition according to claim 1, wherein a Component (A)/[Component(B)+Component(C)] weight ratio, that is, a weight ratio of Component (A) to [Component(B)+Component(C)] is from 0.1 to 2.

5. A detergent used as a skin cleanser or hair shampoo, obtained by mixing the detergent composition as claimed in claim 1 with a surfactant and/or water.

6. A process for preparing a detergent, comprising mixing the detergent composition as claimed in claim 1 with a surfactant and/or water.

7. The process for preparing a detergent according to claim 6, wherein a (the surfactant)/(the detergent composition) weight ratio, that is, a weight ratio of the surfactant to the detergent composition is from 1 to 60.

8. The process for preparing a detergent according to claim 6 or 7, wherein the detergent composition is contained in the entire detergent in an amount of from 0.5 to 12 wt. %.

* * * * *